US012376764B2

(12) United States Patent
Leussler et al.

(10) Patent No.: US 12,376,764 B2
(45) Date of Patent: Aug. 5, 2025

(54) REPOSITIONING METHOD

(71) Applicant: KONINKLIJKE PHILIPS N.V., Eindhoven (NL)

(72) Inventors: Christoph Günther Leussler, Hamburg (DE); Jan Hendrik Wuelbern, Hamburg (DE); Mark Thomas Johnson, Arendonk (BE); Rajendra Singh Sisodia, Bkopal (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 225 days.

(21) Appl. No.: 17/923,010

(22) PCT Filed: May 7, 2021

(86) PCT No.: PCT/EP2021/062122
§ 371 (c)(1),
(2) Date: Nov. 3, 2022

(87) PCT Pub. No.: WO2021/228703
PCT Pub. Date: Nov. 18, 2021

(65) Prior Publication Data
US 2023/0355134 A1 Nov. 9, 2023

(30) Foreign Application Priority Data

May 12, 2020 (IN) .............................. 202041020049
May 26, 2020 (EP) ..................................... 20176540

(51) Int. Cl.
*A61B 5/11* (2006.01)
(52) U.S. Cl.
CPC .................................. *A61B 5/1113* (2013.01)
(58) Field of Classification Search
None
See application file for complete search history.

(56) References Cited

U.S. PATENT DOCUMENTS

2013/0211261 A1* 8/2013 Wang ..................... G16H 50/30
600/476
2014/0070807 A1 3/2014 Biber
(Continued)

FOREIGN PATENT DOCUMENTS

EP 2626718 A1 8/2013
EP 2921100 A1 9/2015

OTHER PUBLICATIONS

PCT International Search Report, International application No. PCT/EP2021/062122, Aug. 2, 2021.

*Primary Examiner* — Ashley K Buran
*Assistant Examiner* — Tommy T Ly
(74) *Attorney, Agent, or Firm* — Larry Liberchuk

(57) ABSTRACT

The present invention relates to patient positioning. In order to improve patient positioning during a scan, an autonomous motion positioner is proposed using a critical range, which may correspond to maximum corrections achievable by the scanner hardware and the maximum tolerable image distortions. The critical range is determined based on one or more machine settings of the medical imaging system. As the machine setting(s) may vary in a given imaging exam, the critical range may dynamically change in response to a change of the machine setting in the given imaging exam. External sensors may measure, via a feedback loop, the deviation from the start position, i.e. the imaging pose position. If patient motion is too large and the motion parameter (e.g. translation and/or rotation) exceeds the determined critical range, then the scan process may be stopped. The autonomous scanner may hold in an idle mode. During that mode, the patient may be guided to retake its original position via a feedback system. A control loop may calculate critical range deviation and the scan process may be continued, if the motion parameter is less than the determined critical range. Accordingly, uncorrectable (Continued)

motion artefacts due to large body movements may be avoided. The motion positioner may be suitable for systems, such as MR, MR-LINAC, computed tomography (CT), and positron emission tomography (PET).

14 Claims, 3 Drawing Sheets

(56) References Cited

U.S. PATENT DOCUMENTS

| | | | |
|---|---|---|---|
| 2015/0323637 A1* | 11/2015 | Beck | G01R 33/56509 600/410 |
| 2016/0000383 A1* | 1/2016 | Lee | G16H 30/20 600/301 |
| 2016/0255966 A1 | 9/2016 | Thomas | |
| 2017/0242088 A1* | 8/2017 | Oh | A61B 5/7221 |
| 2017/0354385 A1 | 12/2017 | Lerch | |
| 2019/0130571 A1* | 5/2019 | Allmendinger | G06T 5/60 |
| 2021/0267488 A1* | 9/2021 | Taghvaeeyan | A61B 5/7221 |

\* cited by examiner

REPOSITIONING METHOD

FIELD OF THE INVENTION

The present invention generally relates to patient positioning, and in particular to a motion positioner for repositioning a body part of a patient when using a medical imaging system to perform a scan, and an associated medical imaging system, method, and computer program element.

BACKGROUND OF THE INVENTION

In the current diagnostic imaging workflow, the patient positioning is typically performed manually. This is physically tiring for staff. The present trend is towards imaging suites requiring fewer human operatives, reducing the number of staff available for patient positioning.

For example, standard magnetic resonance (MR) imaging sessions are performed under full control of experienced staff members. They position the patient on the MR patient support, apply sensors as an ECG unit for cardiac scans, select, adapt and run the specific set of scans, perform some immediate image quality control, archive the images, and dismiss the patient from the MR suite. Because MR sessions are typically relatively long, this represents a large cost factor in radiology. Therefore, more autonomous imaging approaches are desirable, in which at least some of the above steps are automated. Other drivers towards autonomous imaging are generally increasing numbers of MR examinations and a lack of experienced staff in many regions. For example, US 2016/0255966 A1 discusses a system for adjusting a body support including a body support having an adjustable layer and a plurality of sensors, and a processing system in communication with the plurality of sensors and the adjustable layer.

Long exposure times during MR imaging make the images susceptible to patient movements, which may lead to blurred images or so-called ghosting artefacts in which parts of the image are repeated. These artefacts can make a diagnosis impossible, which necessitates either taking the picture again or sedation of the patient to avoid movement. This is where motion correction procedures come into play. The so-called prospective motion correction requires additional motion information, which is still used during the image acquisition to change the imaging parameters so that the image section follows the motion. However, prospective motion techniques adapting the geometry of the MR-acquisition are limited to the compensation of rigid motion events, for example repositioning of the image volume in brain scans. In other anatomies, such as joints or inner organs of abdominal imaging, the deformations may be considerably more complex and not compensable with prospective techniques and require repositioning of the patient to ensure data consistency.

Many patients may find it difficult to keep their arm and legs still during a MR examination. Furthermore, the patient may have the urge to release stress or anxiety via body movements. However, only up to a certain magnitude of displacement, these types of motion can be corrected by the MR itself using prospective motion compensation techniques.

SUMMARY OF THE INVENTION

There may be a need to improve image quality.

The object of the present invention is solved by the subject-matter of the independent claims, wherein further embodiments are incorporated in the dependent claims. It should be noted that the following described aspects of the invention apply also for the motion positioner, the associated medical imaging system, the method, and the computer program element.

According to a first aspect of the present invention, there is provided a motion positioner for repositioning a body part of a patient when using a medical imaging system to perform a scan. The motion positioner comprises an input unit, a processing unit, and an output unit.

The input unit is configured to obtain a first signal indicative of positional information of the body part of the patient that is being imaged in an imaging pose position.

The processing unit is configured to determine a critical range based on a machine setting of the medical imaging system, within which a motion artefact is correctable with the medical imaging system to obtain a medical image with a tolerable image distortion, to detect a change in the obtained first signal indicating a body motion of the patient and to determine whether a deviation of a position of the body part from the imaging pose position of the body part exceeds the determined critical range around the imaging pose position.

The output unit is configured to transmit a control signal to the medical imaging apparatus to cause the medical imaging apparatus to perform an action in dependence upon a determination result.

In other words, an autonomous motion positioner is proposed using a critical range, which may correspond to maximum corrections achievable by the scanner hardware and the maximum tolerable image distortions.

The critical range is determined based on one or more machine settings of the medical imaging system. As the machine setting(s) may vary in a given imaging exam, the critical range may dynamically change in response to a change of the machine setting in the given imaging exam. Taking multi-slice imaging as an example, position of slice and angulation may be set differently for each slice. Therefore, if the machine setting changes from one slice to another, the critical range may change in response to the change of the machine setting. As a further example, for multiparametric MRI, the critical range may change in response to a change of one or more sequence parameters. In this way, the critical range is more accurately defined for each imaging sequence in a given imaging exam.

For example, the machine setting for an MRI system may comprise one or more of: slice-orientation, phase encoding direction, read-out bandwidth, K-space trajectory, and radiofrequency coil being used.

In an example, the critical range may change during an imaging sequence. For multi-slice imaging, the critical range may depend on position of slice and angulation. During different scans, the critical range may be adapted based on the learning from previous scan and/or due to change of behavior of state of patient.

In another example, the critical range may depend on the phase encoding direction. The phase-encoding direction is associated with two major artifacts: wrap-around and flow/motion. Wrap-around (also called aliasing) occurs when the size of the body part imaged exceeds the defined field-of-view (FOV) in the phase-encode direction. This causes anatomy outside the FOV to be folded in over the main part of the image. Flow and motion artifacts are also propagated predominantly in the phase-encode direction. Moving anatomic structures often producing problematic artifacts during MR imaging include the eyes, pharynx (swallowing), heart, lungs, diaphragm, and upper abdominal organs. The phase-encoding direction is usually chosen so that these artifacts do not project over the area of interest. Therefore, the critical range may be adapted in response to a change of the phase encoding direction.

In a further example, the critical range may be adapted in response to a change of the read-out bandwidth. For example, in routine MR imaging, spatial position is assigned along the frequency-encode direction on the basis of resonant frequency. If both water and lipid protons coexist in a voxel, the signal emitted by the lipid protons will have a lower frequency than that of the water protons. Consequently, if the system frequency is set to water, the signal from the lipid protons will appear to have arisen from water protons from another voxel in a lower part of the field. When image intensities are assigned in the final image, therefore, the location of fat protons will be spatially mismapped toward the lower part of the readout gradient field. This mismapping of fat and water pixels results in artifactual white or dark bands, one-to-several pixels in width, on either side of an anatomic object. The size of the Water-fat-shift artifact can be readily computed in advance based on two parameters selected prior to imaging: readout bandwidth and size of the frequency-encode matrix. Reducing the bandwidth per pixel will accentuate this artifact. Thus, the critical range, within which a motion artefact is correctable with the medical imaging system to obtain a medical image with a tolerable image distortion, may also change in response to a change of the read-out bandwidth.

In a further example, the critical range may be dependent on the K-space trajectory, such as Cartesian, spiral, radial, propeller, or echo-planar. The critical range may be defined in terms of k-space, as translational movement corresponds to a phase shift and rotational movement to a rotation in k-space. Transforming the critical range parameter to equivalent k-space parameters is straight forward with Fourier theory and may have the advantage that the acquired data does not need to be reconstructed for evaluation of critical range, which would save time and is important for real-time applications.

In a further example, the radiofrequency (RF) coil grating and fixation (including position) may limit the patient movement and breathing behavior. In this case, a statistical model of patient data using different coils, fixation techniques, and/or mattresses may further serve as an input for the calculation of the critical range.

In a still further example, the patient can freely breathe during imaging. However, for a requested breath hold, the critical range may be dynamically adapted.

Further, for kinematic studies, such as moving bed applications, the critical range may be defined as a complex vector with direction, volume, angle, dynamic parameter, time frequency, and/or phase, and may be dynamically adapted in response to a change of one or more of the above-discussed machine settings.

The critical range may be derived from one or more of the above-discussed machine settings using a pre-trained machine-learning model, such as a neural network (NN). The machine-learning model refers to a suitable algorithm that is trained on the basis of appropriate training data. As will be explained hereafter, a neural-network (NN) model may be used for determining the critical range. However, other machine-learning techniques such as support vector machines, decision trees or other may be used instead of neural networks. The machine learning may provide automatic adaption of the critical range in response to a change of one or more machine settings.

In another example, for cone-beam CT and for a rotating X-ray scanner such as a fixed or mobile X-ray C-arm scanner, the critical range may depend on one or more of the following machine settings: scanner radial movement data, acquisition period, radiation intensity, beam focal diameter, and rotationally moving the X-ray source and the X-ray detector to different intended circumferential positions about an iso-center of the X-ray scanner.

The CT/X Ray source (can also have two sources) is directly controlled by the critical range control output. If critical range is reached for a defined or adaptable time period, the X-Ray source (or sources) can be stopped, reduced in intensity or modulation (phase, intensity) changed.

In a further example, for MR-LINAC the critical range may depend on one or more of the following machine settings: size and position of lesion, intensity of radiation beam, beam diameter, history of radiation dose. The therapy LINAC beam may be controlled by the critical range parameter. If critical range is reached then the MR LINAC beam is stopped and sequence is repeated, if critical range is again in the requested parameter field.

For MR-PET, the critical range may depend on one or more of the following machine settings: size and position of lesion, speed data of patient bed.

External sensors may measure, via a feedback loop, the deviation from the start position, i.e. the imaging pose position, which is used to control the medical imaging apparatus to perform an action, such as interrupting the scanning process, entering into an idle mode, or continuing the scanning process. For example, if patient motion is too large and the motion parameter (e.g. translation and/or rotation) exceeds the determined critical range, then the scan process may be stopped. The autonomous scanner may hold in an idle mode. During that mode, the patient may be guided to retake its original position via a feedback system. A control loop may calculate critical range deviation and the scan process may be continued, if the motion parameter is less than the determined critical range.

Accordingly, uncorrectable motion artefacts due to large body movements may be avoided. The motion positioner may be suitable for systems, such as MR, computed tomography (CT), MR-LINAC (hybrid MR-Radiation therapy) and positron emission tomography (PET). Patient may use the motion positioner during a position simulator mode to learn the feedback response of the system.

According to an embodiment of the present invention, the input unit is configured to receive a third signal indicative of the machine setting of the medical imaging system. The processing unit is configured to re-determine the critical range in response to a change of the third signal.

For example, for multi-slice imaging, position of slice and angulation may be set differently for each slice. Therefore, if the machine setting changes from one slice to another, the processing unit may configured to re-calculate the critical range in response to the change of the machine setting.

For example, multiparametric MRI is a combination of two or more sequences. Each MRI sequence is a particular setting of pulse sequences and pulsed field gradients, resulting in a particular image appearance. Therefore, the processing unit may be configured to re-calculate the critical range in response to a change of one or more sequence parameters.

Thus, in a given imaging exam, the critical range may be dynamically adaptable in response to a change of the machine setting.

According to an embodiment of the present invention, the processing unit is configured to determine the critical range based on patient information.

In an example, the patient information may include BMI (Body Mass Index), contour of patient, and/or patient ventilation volume.

In an example, size and orientation of local organs (lung, liver) from previous patient data may be used as start parameters for critical range.

In this way, the critical range may be personalized, and more accurately determined for a particular patient. According to an embodiment of the present invention, the critical range comprises at least one of:
- a critical distance, if the deviation of a position of the body part from the imaging pose position of the body part comprises a one-dimensional motion vector;
- a critical area, if the deviation of a position of the body part from the imaging pose position of the body part comprises a two-dimensional motion vector; and
- a critical volume, if the deviation of a position of the body part from the imaging pose position of the body part comprises a three-dimensional motion vector.

For example, the critical area may define a two-dimensional area in the plane of the cross section of the bore of an MRI system, inside which motion artefacts can be corrected with a motion compensation technique.

Whilst the patient motion may be a two-dimensional parameter for capturing movement only in the plane of the cross section of the bore, in a more general situation the patient may also move in the direction along the bore. For example, whilst imaging an ankle, the patient raises their knee whilst their ankle retains contact with the table the ankle will primarily move in a direction along the bore. Thus, it is proposed to extend the critical range to also cover patient movement along the bore.

According to an embodiment of the present invention, the control signal comprises an interruption signal configured to be generated when it is determined that the deviation of the position of the body part from the imaging pose position of the body part exceeds the determined critical range around the imaging pose position. The interruption signal is configured to be transmitted to the medical imaging apparatus to cause the medical imaging apparatus to pause a scan process.

In other words, it is proposed to interrupt the scanning process, if the patient motion is too large and the motion parameter exceeds the critical range. The autonomous scanner may hold in an idle mode. In this idle mode, the patient may be guided to retake its original position (i.e. imaging pose position) or a position within the critical range via a feedback system. Alternatively, an actuator arrangement may be coupled to the body part of interest and to effect the movement of the body part.

For example, for an MR-LINAC system the scanning may be set to hold, but also the radiation beam is stopped and resumed if body part is moved inside critical range.

According to an embodiment of the present invention, the control signal comprises a resume signal configured to be generated when it is determined that the body part is moved inside the determined critical range. The resume signal is configured to be transmitted to the medical imaging apparatus to cause the medical imaging apparatus to resume a scan process.

In other words, once the body part of interest is guided to the original position or to a position within the determined critical range, the scan can continue. Accordingly, uncorrectable motion artefacts due to large body movements may be avoided.

According to an embodiment of the present invention, the processing unit is configured to compute a desired movement of the body part for moving the body part back to the imaging pose position or for moving the body part within the determined critical range around the imaging pose position. The output unit is configured to transmit a corrective signal indicative of the desired movement to (i) an actuator arrangement to cause the actuator arrangement to effect the desired movement of the body part; and/or to (ii) an interactive reposition guidance device configured to advise the patient to effect the desired movement of the body part.

For example, the interactive reposition guidance device may advise the patient via e.g. optical, acoustic, haptic signals.

In some cases, the actuator arrangement may comprise a single actuator that is capable of moving the entire patient, such as electronically controlled motor for driving a patient support. In some examples, the actuator arrangement may comprise a multiplicity of actuators in order to reposition only a portion of the patient, or to reposition several parts of the patient simultaneously.

In some examples, one or more actuators may be a part of the patient support used to support the patient during the scanning. In some examples, one or more actuators may be added to the patient support.

According to an embodiment of the present invention, the input unit is configured to obtain, via one or more sensors, a second signal indicative of a prospective indication of motion indicating that a body motion of the patient may happen, which triggers the processing unit to detect the body motion of the patient.

Prospective indications of motion may include e.g. sneeze, face deformation, pain, cough, change of skin colour, eye tracking, etc.

In an example, the second signal may be e.g. a video signal from a video camera or a depth camera monitoring the face expression or the skin of the patient.

In an example, the second signal may be a vital sign of the patient comprised of: galvanic skin conductance, heart rate, or breathing rate that represents a pain level experienced by the patient.

According to a second aspect of the present invention, there is provided a medical imaging system. The medical imaging system comprises:
- a medical imaging apparatus configured to perform a scan to acquire image data of a body part of the patient; and
- a motion positioner as defined in the first aspect and any associated example configured to transmit a control signal to the medical imaging apparatus to cause the medical imaging apparatus to perform an action.

The medical imaging apparatus may comprise imaging or hybrid imaging therapy device.

Examples of the medical imaging apparatus may include, but are not limited to, three-dimensional rotational X-ray (3DRX), CT imaging apparatus, PET imaging apparatus, MR imaging apparatus, and MR-LINAC apparatus.

According to an embodiment of the present invention, medical imaging apparatus is a magnetic resonance imaging device. A B0 map inhomogeneity measurement is used for providing positional information of the body part of the patient that is being imaged. For an MRI system, one solution to provide positional information is to use B0 map inhomogeneity measurement to measure and track reposition. The B0 map for a patient at one position provides a homogeneity field (f1) and the post movement field provides the homogeneity field (f2) when a patient moves and are beyond the critical range, the B0 inhomogeneity distortion may be used to continue measure and guide until it is the acceptable state.

According to an embodiment of the present invention, one or more sensors are configured to obtain a first signal indicative of positional information of the body part of the patient that is being imaged.

In some examples, the one or more sensors may include a three-dimensional (3D) contactless motion scanner using e.g. light detection and ranging (LIDAR), radio detection and ranging (RADAR), or camera based sensor. The 3D camera based sensor may include e.g. stereo based sensor or infrared video sensor.

In some examples, the one or more sensors comprise one or more optical fibres for performing three-dimensional optical shape sensing.

In an example, the one or more sensors comprise one or more optical fibres for performing three-dimensional optical shape sensing.

For example, the one or more optical fibres comprise one or more of:
- a single laser based fibre with shape sensing which is attachable to clothes of the patient along a whole periphery of the clothes;
- an optical fibre that is attachable to a circular radius across clothes of the patient to create an optical sphere or a circular ring during a movement;
- fibre Bragg grating sensors attachable to clothes of the patient to create a thin three-dimensional shape sensing of polyimide thin film skin for a flexible morphing wing.

Optionally, the optical fibres may also be integrated in thin flexible RF coil array.

According to an embodiment of the present invention, the medical imaging system further an actuator arrangement comprising one or more actuators configured to effect a desired movement of the body part in response to a corrective signal transmitted by the motion positioner.

The corrective signal may also be referred to as a control signal, which is used to control the one or more actuators to effect the desired movement.

In an example, the actuator arrangement comprises a plurality of actuators, each of which is configured to move a respective portion of the patient in at least one direction.

In an example, at least one actuator has a form of plate attached to a motor.

In an example, at least one actuator is a robot arm assembly with one or more robot arms configured to move the body part of interest.

In an example, at least one actuator is a resilient member having an inflatable volume positioned adjacent to the body part of interest of the patient that is being imaged. The inflatable volume is configured to be actuated to inflate or deflate to effect the desired movement of the body part of interest.

In an example, the medical imaging system comprises a patient support having a patient support surface for supporting the patient during a medical imaging process. The actuator arrangement is attachable to the patient support.

In an example, the patient support has a plurality of segments along the patient support surface, each segment being adjustable in height and/or inclination.

According to an embodiment of the present invention, the medical imaging system comprises an interactive reposition guidance device configured to advise the patient to effect a desired movement of the body part in response to a corrective signal transmitted by the motion positioner.

The interactive reposition guidance device may provide audible or visible signals.

According to a third aspect of the present invention, there is provided a method for repositioning a body part of a patient when using a medical imaging system to perform a scan, comprising:
- obtaining, via an input device, a first signal indicative of positional information of the body part of the patient that is being imaged in an imaging pose position;
- detecting, by a processor, a change in the obtained first signal indicating a body motion of the patient;
- determining, by the processor, a critical range based on a machine setting of the medical imaging system, within which a motion artefact is correctable with the medical imaging system to obtain a medical image with a tolerable image distortion, and whether a deviation of a position of the body part from the imaging pose position of the body part exceeds the determined critical range around the imaging pose position; and
- transmitting, via an output device, a control signal to the medical imaging apparatus to cause the medical imaging apparatus to perform an action in dependence upon a determination result.

Optionally, the control signal may comprise an interruption signal configured to be generated when it is determined that the deviation of the position of the body part from the imaging pose position of the body part exceeds the determined critical range around the imaging pose position. The interruption signal is configured to be transmitted to the medical imaging apparatus to cause the medical imaging apparatus to pause a scan process.

Optionally, the control signal may comprise a resume signal configured to be generated when it is determined that the body part is moved inside the determined critical range. The resume signal is configured to be transmitted to the medical imaging apparatus to cause the medical imaging apparatus to resume a scan process.

According to another aspect of the present invention, there is provided a computer program element comprising instructions which, when executed by a computer processor, causes the computer processor to perform the steps of the third aspect and any associated example.

As used herein, the term "unit" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

The term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs). These and other aspects of the present invention will become apparent from and be elucidated with reference to the embodiments described hereinafter.

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

During a clinical imaging sequence, the patient may move due to discomfort, relax stress, or tension. This may result in a dislocation of the imaging volume, which may have one of the two following outcomes. Either the sequence is restarted and thus overall scanning time is increased, or the resulting image quality may be degraded down to a level, which renders the image undiagnostic. Both cases are undesirable and induce additional costs.

To this end, according to a first aspect of the present disclosure, there is provided a motion positioner 10 for repositioning a body part of a patient when using a medical imaging system to perform a scan. The motion positioner 10 comprising:

an input unit 12;
a processing unit 14; and
an output unit 16.

The input unit 12 is configured to obtain a first signal indicative of positional information of the body part of the patient that is being imaged in an imaging pose position.

The processing unit 14 is configured to determine a critical range based on a machine setting of the medical imaging system, within which a motion artefact is correctable with the medical imaging system to obtain a medical image with a tolerable image distortion, to detect a change in the obtained first signal indicating a body motion of the patient and to determine whether a deviation of a position of the body part from the imaging pose position of the body part exceeds a determined critical range around the imaging pose position.

The output unit 16 is configured to transmit a control signal to the medical imaging apparatus to cause the medical imaging apparatus to perform an action in dependence upon a determination result.

The medical imaging system may be e.g. 3DRX, CT imaging system, PET imaging system, MR imaging system, MR LINAC imaging system, or MR-PET system. To facilitate understanding of the system and method described herein, an MR imaging system will be described henceforth as the example of medical imaging system.

Figure 1:
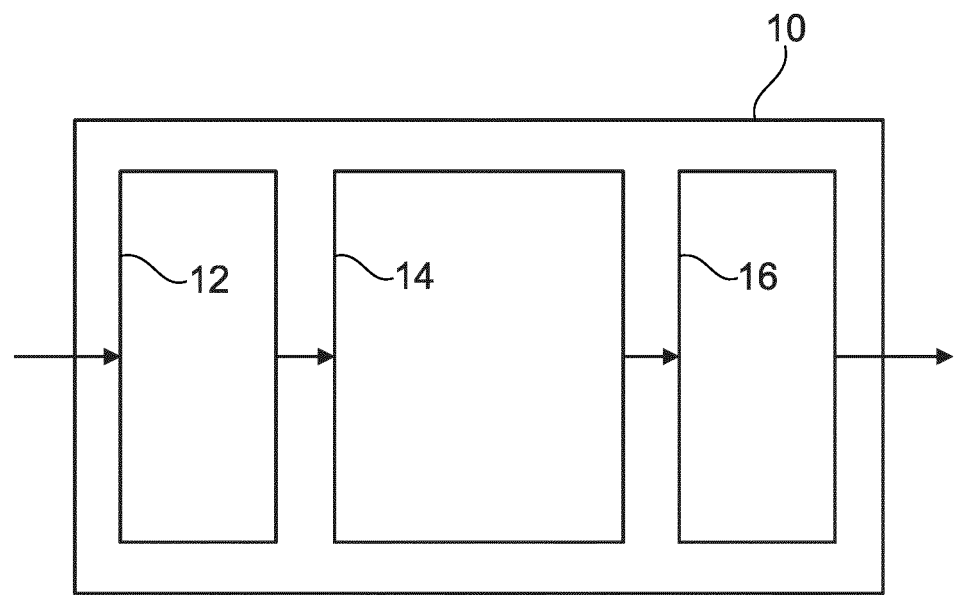
FIG. 1 schematically illustrates a device according to a first aspect of the present disclosure.

FIG. 1 schematically illustrates a device 10 according to the first aspect of the present disclosure. The motion positioner 10 may be implemented as an embedded computing device or on a personal computer, for example.

The input unit 12 is configured to obtain a signal indicative of positional information of the body part of interest of the patient that is being imaged in an imaging pose position relative to an imaging device.

In an example, the first signal may be a video feed having a field of view that covers the body part of interest received e.g. from a three-dimensional contactless motion scanner using e.g. light detection and ranging (LIDAR), radio detection and ranging (RADAR), or camera based sensor.

In another example, the first signal may be a signal obtained using three-dimensional optical shape sensing. Optical shape sensing is primarily used for guiding a catheter in a blood vessel in a three-dimensional space. Direct femtosecond laser based processing of Bragg gratings into the core and the cladding of an optical fibre makes it possible using just a single standard one-core optical fibre for three-dimensional shape monitoring with the advantage of no need for additional optics and they are immune to magnetic fields. In a first example, single laser based fibres with shape sensing may be woven into the patient clothes along the whole periphery or woven in thin ultra-lightweight RF coils that can provide a three-dimensional shape sensing in real time. The three-dimensional envelop may calculate the current position before the patient movement and post the movement. The difference of the catch radius can be calculated based on the three-dimensional envelopes. In a second example, optical fibres may be woven into circular radius across the clothes to create the optical spheres/circular rings during movements that can be detected and identified if they are beyond the critical range. In a third example, it is proposed to create a thin three-dimensional shape sensing of polyimide thin film skin for a flexible morphing wing using fibre Bragg grating (FBG) sensors and attach to the patient clothes and coil depending on the use case. The four-dimensional shape-sensing envelope may provide an accurate measurement of patient movement and provide a general feedback loop for reposition.

Another solution to provide positional information is to use B0 map inhomogeneity measurement to measure and track reposition. The B0 map for a patient at one position provides a homogeneity field (f1) and the post movement field provides the homogeneity field (f2) when a patient moves and are beyond the critical range, the B0 inhomogeneity distortion may be used to continue measure and guide until it is the acceptable state.

Optionally, the input unit 12 may be configured to obtain, via one or more sensors, a second signal indicative of a prospective indication of motion, e.g. sneeze, face deformation, pain, cough, etc., indicating that a body motion of the patient may happen, which triggers the processing unit 14 to detect the body motion of the patient.

The input unit 12 is, in an example, implemented as an Ethernet interface, a USB™ interface, a wireless interface such as a WiFi™ or Bluetooth™, 5G or 6G protocol or any comparable data transfer interface enabling data transfer between input peripherals and the processing unit 14.

The processing unit 14 is configured to detect a change in the obtained signal indicating a body motion of the patient.

For example, the body motion may be translational or rotational. The body motion may be rigid or non-rigid. The body motion may be periodic or un-periodic. For MRI imaging, un-periodic bulk motion may comprise rigid translation and rotation of the part of the body that is being imaged, and is mostly caused by voluntary or involuntary patient movement.

For an acquired two-dimensional MR image, the motion may be further classified as in-plane motion or through-plane motion.

For example, the body motion may vary in timing and amplitude.

The processing unit 14 is further configured to determine a critical range based on a machine setting of the medical imaging system, within which a motion artefact is correctable with the medical imaging system to obtain a medical image with a tolerable image distortion, to determine whether a deviation of a position of the body part from the imaging pose position of the body part exceeds the determined critical range around the imaging pose position.

The critical range may be maximum corrections achievable by the scanner hardware and the maximum tolerable image distortions. For example, MRI motion compensation techniques may be used to indicate that a k-space segment, should be reacquired when motion is detected or, since the exact rotational and translational motion can quite accurately be deduced, to adapt the pulse sequence such that it still acquires the original volume of interest.

For MR imaging, the maximum corrections achievable by the scanner hardware and the maximum tolerable image distortions are dependent on the particular imaging sequence and application. For example, the critical range may be defined as a geometrical rotation or translation, but also based on other related parameters based on pulse sequence parameters, such as limit of system power of gradient, RF and timing. The MM technique is limited and the threshold for the critical range is defined if the image is correctable or not. The limitations are defined by the physical system parameters of the MRI machine and the safe parameter space of the pulse sequence.

For example, the critical range may change in response to a change of one or more of the following machine settings for MM: slice-orientation, phase encoding direction, read-out bandwidth, K-space trajectory, and radiofrequency coil being used.

In an example, the critical range may depend on position of slice and angulation. During different scans, the critical range may be adapted based on the learning from previous scan or due to change of behavior of state of patient.

In an example, the critical range may change in response to a change of the phase encoding direction, which is usually chosen so that these artifacts do not project over the area of interest.

In an example, the critical range may depend on the read-out bandwidth. The size of the Water-fat-shift artifact can be readily computed in advance based on two parameters selected prior to imaging: readout bandwidth and size of the frequency-encode matrix. Reducing the read-out bandwidth per pixel will accentuate this artifact. Thus, the critical range, within which a motion artefact is correctable with the medical imaging system to obtain a medical image with a tolerable image distortion, may also change in response to a change of the read-out bandwidth.

In a further example, the critical range may be defined in terms of k-space, as translational movement corresponds to a phase shift and rotational movement to a rotation in k-space. Transforming the critical range parameter to equivalent k-space parameters is straight forward with Fourier theory and may have the advantage that the acquired data does not need to be reconstructed for evaluation of critical range, which would save time and is important for real-time applications.

In a further example, a statistical model of patient data using different RF coils, fixation techniques, and mattresses may further serve as an input for the calculation of the critical range.

For kinematic studies, such as moving bed applications, the critical range may be defined as a complex vector with direction, volume, angle, dynamic parameter, time frequency, and/or phase, and may be dynamically adapted in response to a change of one or more machine settings.

In another example, for cone-beam CT and for a rotating X-ray scanner such as a fixed or mobile X-ray C-arm scanner, the critical range may depend on one or more of the following machine settings: scanner radial movement data, acquisition period, radiation intensity, beam focal diameter, and rotationally moving the X-ray source and the X-ray detector to different intended circumferential positions about an iso-center of the X-ray scanner.

The CT/X Ray source (can also have two sources) is directly controlled by the critical range control output. If critical range is reached for a defined or adaptable time period, the X-Ray source (or sources) can be stopped, reduced in intensity or modulation (phase, intensity) changed.

In a further example, for MR-LINAC the critical range may depend on one or more of the following machine settings: size and position of lesion, intensity of radiation beam, beam diameter, history of radiation dose. The therapy LINAC beam may be controlled by the critical range parameter. If critical range is reached then the MR LINAC beam is stopped and sequence is repeated, if critical range is again in the requested parameter field.

For MR-PET, the critical range may depend on one or more of the following machine settings: size and position of lesion, speed data of patient bed.

Optionally, the critical range may change in response to a change of patient information, such as a change of BMI, contour of patient, and/or patient ventilation volume. Further, size and orientation of local organs (lung, liver) from previous patient data may also serve as an input for the calculation of the critical range. As a further example, the critical range may depend on the prone supine positioning of the patient as organs are differentially mechanically coupled with respect to motion and breathing.

The input unit 12 may be configured to receive a third signal indicative of the machine setting of the medical imaging system. The processing unit 14 may be configured to re-determine the critical range in response to a change of the third signal.

In an example, for multi-slice imaging, position of slice and angulation may be set differently for each slice. Therefore, if the machine setting changes from one slice to another, the processing unit may configured to re-calculate the critical range in response to the change of the machine setting.

In an example, multiparametric MRI is a combination of two or more sequences. Each MRI sequence is a particular setting of pulse sequences and pulsed field gradients, resulting in a particular image appearance. Therefore, the processing unit may be configured to re-calculate the critical range in response to a change of one or more sequence parameters.

The critical range may be derived from one or more machine settings, optionally with patient information, using a pre-trained machine-learning model, such as a neural network (NN). The machine learning may provide automatic adaption of the critical range parameters settings in response to a change of one or more machine settings.

The machine-learning model may be operable in two modes: "training mode/phase" and "deployment mode/phase". In training mode, an initial model of the data-driven model is trained based on a set of training data to produce a trained data-driven model. In deployment mode, the pre-trained data-driven model is fed with non-training, newly acquired image data, to operate during normal use.

The training mode is preferably supervised, that is, is based on annotated training data. For each pair, one item is the training input data and the other item is target training data known a priori to be correctly associated with its training input data item. This association defines the annotation and is preferably provided by a human expert. The training pair includes a machine setting(s) and optional patient information as training input data, and associated with each training input, is target of annotation for the critical range (e.g. critical distance, critical area, and critical volume).

Taking NN as an example, in training mode, preferably multiple such pairs are applied to the input layer to propagate through the NN until an output emerges at an output layer. Initially, the output is in general different from the target. During the optimization, the initial configuration is readjusted so as to achieve a good match between input training data and their respective target for all pairs. The match is measured by way of a similarity measure, which can be formulated in terms of on objective function, or cost function. The aim is to adjust the parameters to incur low cost, that is, a good match. Once the machine-learning model is trained with sufficient annotated training data, the machine-learning model may be used to automatically derive the critical range from one or more machine settings in deployment mode. Patient information may serve as optional input for the calculation of the critical range.

In this way, the machine learning provides automatic adaptation of the critical range parameters setting.

In an example, the critical range may be a critical distance, if the deviation of a position of the body part from the imaging pose position of the body part comprises a one-dimensional motion vector.

In an example, the critical range may be a critical area, if the deviation of a position of the body part from the imaging pose position of the body part comprises a two-dimensional motion vector. For example, the critical area may define a two-dimensional area in the plane of the cross section of the bore of an MRI system, inside which motion artefacts can be corrected with a motion compensation technique.

In an example, the critical range may be a critical volume, if the deviation of a position of the body part from the imaging pose position of the body part comprises a three-dimensional motion vector. Whilst the patient motion may be a two-dimensional parameter for capturing movement only in the plane of the cross section of the bore, in a more general situation the patient may also move in the direction along the bore. For example, whilst imaging an ankle, the patient raises their knee whilst their ankle retains contact with the table the ankle will primarily move in a direction along the bore. In this example, it is proposed to extend the above approach to also cover patient movement along the bore. For example, instead of a two-dimensional area it will now be required to consider a three-dimensional volume defined as e.g. the radius of a sphere. In this case, any movement, which remains inside this sphere, will not require intervention of the system of this patent as the motion can be corrected by the image processing. However, any vector movement in three dimensions greater than the radius of the sphere may trigger the repositioning sequence as described above. The above description of a sphere of movement and associated movement vector of uniform length assume that the system is equally capable of correcting for motion in all directions. However, in reality the system may be configured to correct more motion in one direction (for example along the bore) than in another direction (for example perpendicular to the axis of the bore). Consequently, the system may be more tolerant to motion in one direction compared to the other direction. Consequently, instead of the sphere shaped volume, the critical motion volume may be described as an ellipse form (i.e. a stretched sphere) with two radii (i.e. major and minor axis). In other words, the motion parameter radius will then be larger for one direction of motion than the other. More in general, the critical range may be defined by the radius of the ellipse in the direction of the vector of the motion. If the capability of the system to correct for motion is different in all three directions, the sphere may be distorted to a flattened elliptical form, i.e. a sphere stretched differently in two directions.

Thus, the processing unit 14 may comprise a general-purpose processing unit, a graphics processing unit (GPU), a microcontroller and/or microprocessor, a field programmable gate array (FPGA), a digital signal processor (DSP), and equivalent circuitry, alone or in combination. Furthermore, such processing unit(s) 14 may be connected to volatile or non-volatile storage, display interfaces, communication interfaces and the like as known to a person skilled in the art. A skilled person will appreciate that the implantation of the processing unit 14 is dependent on the compute intensity and latency requirements implied by the selection of signals used to represent positional information in a particular implementation.

The output unit 16 is configured to transmit a control signal to the medical imaging apparatus to cause the medical imaging apparatus to perform an action in dependence upon a determination result. The medical imaging apparatus may comprise imaging or hybrid imaging therapy device.

For example, the control signal may comprise an interruption signal configured to be generated when it is determined that the deviation of the position of the body part from the imaging pose position of the body part exceeds the determined critical range around the imaging pose position. The interruption signal is configured to be transmitted to the medical imaging apparatus to cause the medical imaging apparatus to pause a scan process.

For example, the control signal may comprise a resume signal configured to be generated when it is determined that the body part is moved inside the determined critical range. The resume signal is configured to be transmitted to the medical imaging apparatus to cause the medical imaging apparatus to resume a scan process.

Optionally, the processing unit 14 may be configured to compute a desired movement of the body part for moving the body part back to the imaging pose position or for moving the body part within the determined critical range around the imaging pose position. The output unit 16 may be configured to transmit a corrective signal indicative of the desired movement to an actuator arrangement to cause the actuator arrangement to effect the desired movement of the body part.

The desired movement of the body part and/or the desired movement of the imaging device may be a desired translational and/or rotational movement.

For example, the desired movement of the body part may be determined based on a model-based approach. In this model-based approach, a three-dimensional position grid of a patient along with all the attachments may be created. A reference of this three-dimensional position may be created and continuously adapted based on the patient movements. If the patient movement is beyond the critical range and will result in image artefacts, the actuator system needs to be activated to put the body part of interest back in the reference position (or reference range). Since the current position of body parts need to move back to original position, it may not be linear position of the actuators as it may hurt the patient due to unnatural movement trajectory.

Therefore, it is proposed to capture the movement trajectory of the patient movements so that the patient position is followed in substantially exact reverse trajectory to the possible extent.

In a first example, the position matrix and the movement trajectory may be provided as a feedback to control the actuator arrangement as described below.

In a second example, the three-dimensional position matrix may be superimposed on the three-dimensional camera content to create a three-dimensional model. During the movement, the three-dimensional model gets deformed. When the movements are such that the image artefacts start occurring, the deformed model will be used as an input to control the actuator arrangement such that motion artefacts can be corrected. A skilled person will appreciate that many techniques in three-dimensional animation applications can be used for building the three-dimensional model.

Optionally, the medical imaging system is configured to perform a sequence of scans in accordance with a sequence of scan protocols. The processing unit 14 is configured to compute, for each scan, a respective desired movement of the body part of interest for repositioning the body part of interest for the respective scan. The output unit 16 is configured to transmit, for each scan, a respective control signal to the actuator arrangement to cause the actuator arrangement to effect the respective desired movement of the body part of interest. In other words, the dynamic repositioning of the patient may also be applied to optimize a sequence of scan-protocols with respect to the optimized positioning of the patient. E.g. during the first scan has to be positioned in a slightly different way to achieve the best image quality compared to a second scan. In conventional imaging, a staff member would stop the scan, reposition the patient, and start a second scan. With the help of the actuator arrangement, a most preferable position could be selected for the first scan, which would allow for minimum motion of the patient and best positioning. After the first scan, the position of the patient could be tuned for the second scan with minimum risk of motion for the second scan and always with best patient guidance.

Optionally, the processing unit 14 may be configured to compute a desired movement of the body part for moving the body part back to the imaging pose position or for moving the body part within the determined critical range around the imaging pose position. The output unit 16 may be configured to transmit a corrective signal to an interactive reposition guidance device configured to advise the patient, e.g. via audible instructions (e.g. "moving forward", "moving to the left", "stop") or visible instructions e.g. on a display, to effect the desired movement of the body part.

According to a second aspect of the present disclosure, there is provided a medical imaging system 100. The medical imaging system 100 comprises:

a medical imaging apparatus 20 configured to perform a scan to acquire image data of a body part of the patient; and a motion positioner 10 as defined in the first aspect and any associated example configured to transmit a control signal to the medical imaging apparatus to cause the medical imaging apparatus to perform an action.

Figure 2:
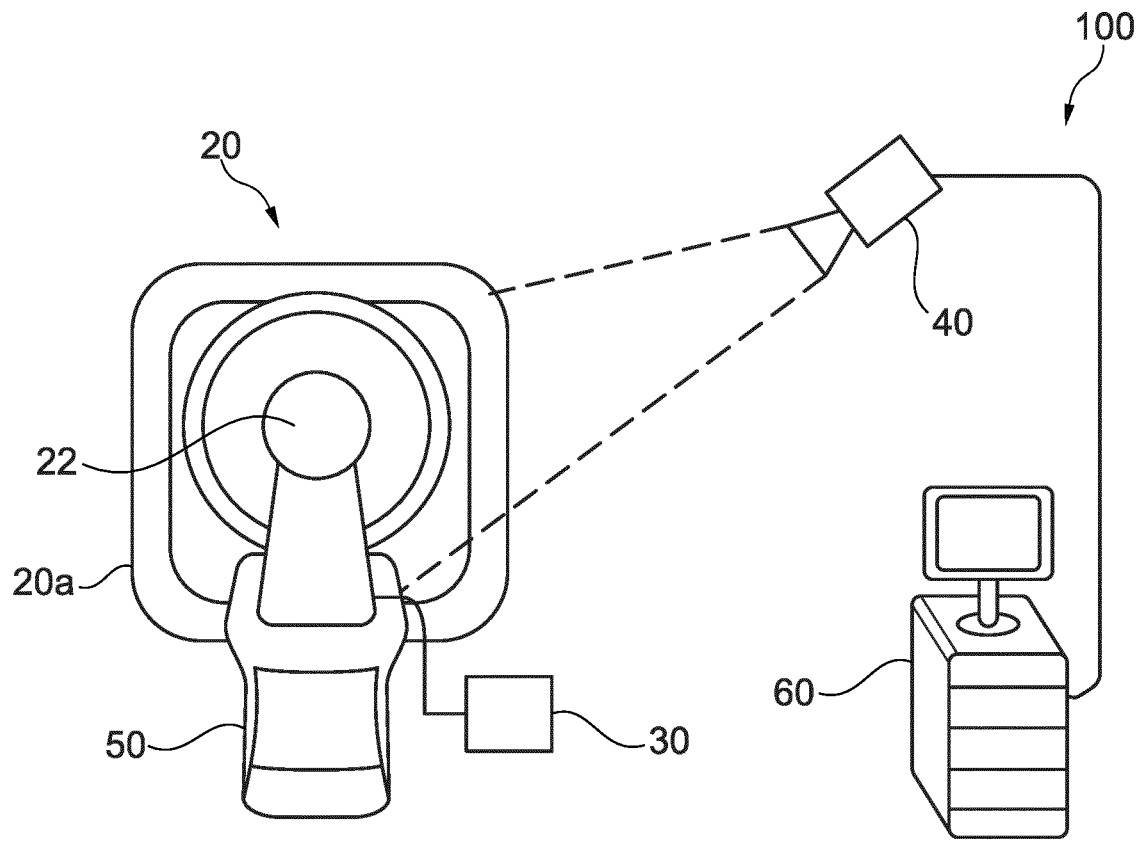
FIG. 2 schematically illustrates a medical imaging system according to a second aspect of the present disclosure.

FIG. 2 schematically illustrates a medical imaging system 100 according to the second aspect of the present disclosure. In this example, the medical imaging system 100 comprises a medical imaging apparatus 20, an actuator arrangement 30, a patient support 50, and a scan control device 60.

The medical imaging apparatus 20 is configured to perform a scan to acquire image data of a body part of interest (e.g. head, neck, knee, etc) of a patient. Examples of the medical imaging apparatus 20 may include, but are not limited to, an MR imaging apparatus, a PET imaging apparatus, or a CT imaging apparatus.

To facilitate understanding of the system and method described herein, an MR imaging apparatus 20*a* will be described henceforth as the example of medical imaging apparatus 20. The imaging apparatus 20*a* produces a polarizing magnetic field in a region commonly referred to as the magnet "bore" 22. The images to be produced by the MR imaging apparatus 20*a* are prescribed by selecting an appropriate nuclear magnetic resonance (NMR) imaging pulse sequence to be executed by a pulse generator. Location and orientation of the slices or three-dimensional region to be imaged are also prescribed and are determined by the particular patient anatomy that the physician wants to see during the procedure being performed. A scan control device 60 may be manipulated by the physician to "point" at specific patient anatomy and this "pointing" is sensed by the tracking coils and used to update the scan parameters. As a result, an updated image is acquired, reconstructed and produced on display, which depicts the anatomy of interest to the physician. The physician can thus move scan control device 60 over and around the patient and the MR imaging apparatus continuously updates the image on display to depict the anatomy of interest.

The actuator arrangement 30 comprises one or more actuators configured to move the body part of interest. Alternatively or additionally, the actuator arrangement 30 comprises one or more actuators configured to move an imaging device, e.g. patient coil, of the medical imaging system.

The scan control device 60 may comprise a motion positioner according to the first aspect, which is configured to transmit a control signal to the actuator arrangement 30 to cause the actuator arrangement to effect the desired movement of the body part of interest and/or to effect the desired movement of the imaging device (e.g. patient coil).

In an example, the motion positioner may receive video signals from a video camera 40. The positional information of the body part of interest of the patient may be obtained by processing the signals received from the video camera 40. If the video camera receives an image of a patient changing shape indicating a body motion of the patient, then the motion positioner determines whether a deviation of a position of the body part from the imaging pose position of the body part exceeds the determined critical range around the imaging pose position and transmits a control signal to the medical imaging apparatus to cause the medical imaging apparatus 20 to perform an action (e.g. interrupting the scanning process, entering into an idle mode, or continuing the scanning process) in dependence upon a determination result.

Optionally, the scan control device 60 may be configured to be an interactive reposition guidance device which provides e.g. audible or visible signals advising the patient how to modify position and posture.

Optionally, the motion positioner may send a control signal to the actuator arrangement 30 to cause the actuator arrangement 30 to effect the desired movement of the body part of interest and/or to effect the desired movement of the imaging device.

In the following, specific repositioning approaches will described if the patient moves in either the direction along the bore of the imaging machine, in the vertical direction in the bore, or in the lateral direction in the bore.

Example 1: Motion Along the Bore of the System (x-Axis)

In this example, motion of a body part of the patient being imaged along the bore of the scanner, which we will call the x-direction, is considered. This may occur, for example, whilst imaging an ankle: if the patient raises their knee whilst their ankle retains contact with the table the ankle will primarily move in a direction along the bore.

In this case, it is proposed to monitor the motion along the bore of the part of the patient being imaged using e.g. 3D LIDAR, 3D RADAR, or 3D camera.

In most cases, the patient support is also responsible for movement of the patient in and out of the bore and does this with an electronically controlled motor. Hence, in an example, it is proposed to re-use this feature to carry out the compensation of the motion along the bore. Specifically, if the system notices the body part being imaged has moved a distance x along the bore, the system responds by moving the entire patient support by a distance −x, whereby the body part being imaged remains stationary.

In another example, it is proposed to provide a multiplicity of actuators on top of the patient support, each of which supports a portion of the patient. The actuators may have the form of plates attached to linear or multi-axis motors, which may advantageously have a thin profile such that the space within the bore is only very marginally reduced. For example, a first actuator may support the left ankle, whilst a second actuator the right ankle. In this case, if motion is only detected in one of the ankles of the patient, only this actuator is required to correct the position. This has the advantage that if both ankles are being scanned together, the other ankle (which has not moved) remains correctly imaged.

Example 2: Motion in the Horizontal Direction Perpendicular to the Axis of the Bore (y-Axis)

In this example, motion of a body part of the patient being imaged in the horizontal direction perpendicular to the axis of the bore of the scanner, which we will call the y-direction, is considered. This may occur, for example, whilst imaging any peripheral limbs or even the torso if the patient twists. In this case, it is proposed to monitor the motion in the horizontal direction perpendicular to the axis of the bore of the scanner of the part of the patient being imaged using e.g. 3D LIDAR, 3D RADAR, or 3D camera. Specifically, if the system notices the body part being imaged has moved a distance y in the horizontal direction perpendicular to the axis of the bore of the scanner, the system responds by moving the part of the patient being imaged by a distance −y, whereby the body part being imaged remains stationary.

In an example, at least one actuator used to move the patient may have the form of plates attached to a linear or multi-axis motor attached to the top of the patient support, which may advantageously have a thin profile such that the space within the bore is only very marginally reduced.

In another example, at least one actuator may have the form of an inflatable volume positioned adjacent to the portion of the patient being imaged. If the patient moves towards the volume, it is inflated to cause the patients limb to be moved back towards its original position. In this case, a further approach to detection of motion could be a pressure sensor or a proximity sensor attached to the inflatable volume which initiates the actuation (i.e. the inflation of the volume). Similarly the same effect can also be achieved by deflating an inflatable volume on the other side of the body part—or indeed by doing both actions together which may have the additional advantage that the position of the limb above the table remains relatively unchanged.

In a further example, it is possible to provide a multiplicity of actuators on top of the patient support, each of which supports a portion of the patient. For example a first actuator may actuate the left leg, whilst a second actuator the right leg. In this case, if motion is only detected in one of the leg of the patient, only this actuator is required to correct the position. This has the advantage that if both legs are being scanned together, the other leg (which has not moved) remains correctly imaged.

Example 3: Motion in the Vertical Direction Perpendicular to the Axis of the Bore (z-Axis)

In this example, motion of a body part of the patient being imaged in the vertical direction perpendicular to the axis of the bore of the scanner (which we will call the z-direction) is considered. This can occur for example whilst imaging any peripheral limbs or even the torso if the patient twists. In this case, it is proposed to monitor the motion in the vertical direction perpendicular to the axis of the bore of the scanner of the part of the patient being imaged. Specifically, if the system notices the body part being imaged has moved a distance z in the horizontal direction perpendicular to the axis of the bore of the scanner, the system responds by moving the part of the patient being imaged by a distance −z, whereby the body part being imaged remains stationary.

In an example, at least one actuator used to move the patient may have the form of plates attached to a linear or multi-axis motor attached to the top of the patient support and capable of moving the plate perpendicular to the support, which may advantageously have a thin profile such that the space within the bore is only very marginally reduced.

In another example, at least one actuator may have the form of an inflatable volume positioned under the portion of the patient being imaged.

For the vertical movement, it is in necessary that the movement of the actuators can also be towards the patient support. As the patient support is usually a fairly rigid structure this requires that the actuators may be pre-actuated in the reference condition. Specifically, if the actuators are initially positioned z0 cm above the patient support, a movement of the patient's body part being imaged by z1 cm away from the support can be compensated by reducing the actuation of the actuator by z1 cm (i.e. remaining actuation is z0−z1 cm). Clearly a movement of the patient back towards the support by z2 cm (z2<z1) can further be compensated by increasing the actuation be z2 cm (i.e. total actuation (z0−z1+z2 cm) etc.

In another example, it is proposed to provide a multiplicity of actuators on top of the patient support, each of which supports a portion of the patient. For example a first actuator may actuate the left leg, whilst a second actuator the right leg. In this case, if motion is only detected in one of the leg of the patient, only this actuator is required to correct the position. This has the advantage that if both legs are being scanned together, the other leg (which has not moved) remains correctly imaged.

Example 4: Complicated Motion

If a more complicated motion is detected, e.g. a motion at an angle to the bore of the system, it is proposed to compensate for the vector component of the motion in the horizontal direction perpendicular to the axis of the bore of the scanner (i.e. the y direction). Other motions vectors in directions perpendicular to the y direction must be compensated using different approaches as described above.

In this example and also in the above examples, the actuator—in some cases also called linear motor—has to be designed and integrated into the patient table and imaging system in a way that the image quality is not degraded due to the actuator components itself. In addition, the influence of the different components of the actuator system in the different positions should have minimal influence on the image quality. For an MR imaging system this is different compared to a CT system. E.g. in CT there should be no x-ray absorbing material moved inside the volume of interest (scanning volume) that would influence the image quality, the scattering and or the absorption leading to image artefacts. Because of that e.g. pneumatic systems with air or low influencing liquids might be preferred for the motion actuators. Otherwise, translation elements from the motors outside the imaging volume might be used and selected in a way that the image influencing material and geometry selection is well adapted to the imaging modality.

Example 5: Multi-Purpose Actuator

The above-described examples are each designed to serve for motion into one of three dimensions. In general, all three types need to be present in the bore of the imaging system to account for patient motion. This raises the problem that some bore space may be occupied by these various actuators.

In this example, it is proposed to use one single type of actuator that serves to move the patient in all directions. This actuator may be constructed similar as the arm of an industry robot arm used in manufacturing. It may be equipped with a hand-like tool that can grab and release or nudge any part of the patient gently into the correct position. This robot arm may be suspended on a rail inside the bore so that it can slide inside, act, and slide out of the bore again if this is required for imaging. The arm may as well remain inside the bore if it is MR compatible. Two such robot arms may be used for actions that require two "hands" to reposition the patient. They may slide into the bore from foot and head end to save space. The data that encode the current and required patient shape and position are determined from any type of suitable three-dimensional sensor, including the imaging system itself.

The imaging process may be paused after some gross motion has been detected. The actuators are used to reposition the patient. The imaging process may then be resumed. Note, that fully automatic and precise actuators will allow such repositioning of the patient during a single imaging MR, i.e. (k-space or CT projection) data of the same scan can be used to reconstruct a larger set of image slices or an image volume.

Example 6: Segmented Patient Table

In this example, it is proposed to use a segmented patient table with an array of actuators. Each of the segments may be adjusted in height and inclination (angulation). Optionally, individual segments of the table may be equipped with removable flexible pads.

Figure 3:
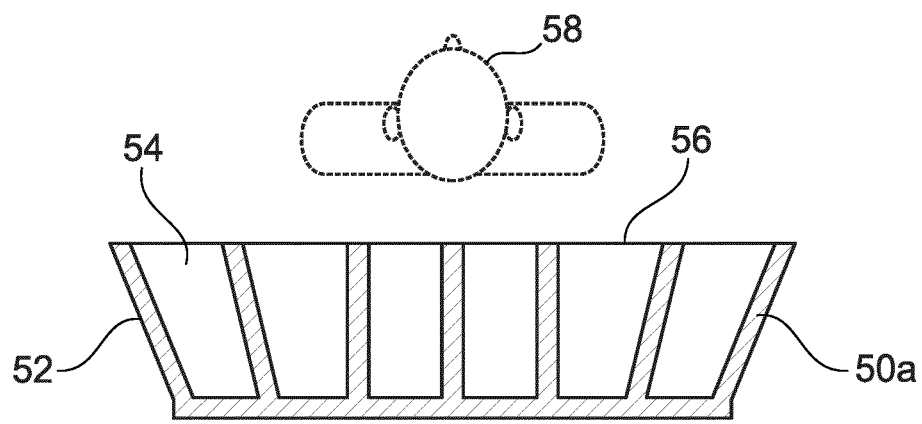
FIG. 3 schematically illustrates a side view of an exemplary segmented patient table.

FIG. 3 schematically illustrates a side view of an exemplary segmented patient table 50a with a lamellar structure made from a resilient airtight rubber, or plastic, for example. The array of lamellae 52 form flexible or semi-rigid walls enclosing inflatable chambers 54. The inflatable chambers may be progressively inflated to enable a patient support surface 56 of the segmented patient table 50a to be substantially planner. The inflatable chambers 54 may be locally pressurized to cause one or more lamellae 52 to expand outwards, thus adjusting the local height to move a body part of interest of a patient 58. In an example, the segmented patient table 50a may be a fluid actuated segmented patient support.

The patient has to stay in a position that becomes uncomfortable for long imaging sequences. One example would be lying on the side for a prolonged duration of time. Depending on the patient anatomy, this can put a lot of pressure on the hip and become painful. In some examples, a pressure or weight sensors may be added to each individual segment. For example, each actuator plate may be equipped with an individual pressure sensor, measuring weight of patient and dynamic motion response of patient. If patient is locally dynamically moving, a feedback algorithm calculates a medium pressure. Individual preformation of actuator array for a patient with an individual local pain region (e.g. ulcer). The data of the pain region of the patient may be captured before the scan and coordinates are transmitted to the control of the segmented patient table. This makes it possible to determine a two-dimensional map of distributed weight and determine regions of high pressure. The individual segments may be adjusted such that local high pressure peaks are removed and the patient feels less pain and can thus stay longer in the imaging pose position.

Instead of moving the patient, the individual segments can change the position of the patient coil and adapt the position to the individual geometry of the patient.

Typically the patient is rested on a mattress. In some examples, this mattress may have local recess, which fit to the individual segments of the patient table.

In case a RF coil is positioned on the patient table, all sensors below the coil chassis remain inactive or set to a certain position, so that segments act as a fixation of the coil itself.

For certain clinical applications, dynamic scanning of the segmented patient table 50a may be used to investigate joints. The MRI scan is directly linked with the individual segments. During a fast sequence (dynamic scanning) the patient table 50a may change its geometry and thus the position in a defined way. MRI scan and dynamic segmented table forming is planned using a SW interface. The system may also allow dynamically reposition the patient during a dynamic scan if patient abnormal movement is detected. More specifically the system dynamically reposition the patient body during a scan if the patient movement exceeds a given critical range, as described above. For MRI imaging of head and neck and partly spine a dedicated head neck coil is located on the patient table. In that case, the individual segments of the patient table cannot be used to compensate motion during MRI sequence. In this case, it is also proposed to integrate individual segments in the housing of head neck coil, or other coil like knee coil, mamma coil, etc. The individual segments of the coil and the segments of the patient bed may be controlled together by the same controller to compensate for the complex body motion of the patient.

For all cases described above, when some image influencing effects would be expected a pre-performed calibration measurement would improve the image-quality as the positions of the actuator elements would be known for each setting.

According to a third aspect of the present disclosure, there is provided a method 200 for repositioning a body part of a patient when using a medical imaging system to perform a scan. The method comprises:

obtaining 210, via an input device, a first signal indicative of positional information of the body part of the patient that is being imaged in an imaging pose position;

detecting 220, by a processor, a change in the obtained first signal indicating a body motion of the patient;

determining 230, by the processor, whether a deviation of a position of the body part from the imaging pose position of the body part exceeds a given critical range around the imaging pose position within which a motion artefact is correctable with the medical imaging system to obtain a medical image with a tolerable image distortion; and transmitting 240, via an output device, a control signal to the medical imaging apparatus to cause the medical imaging apparatus to perform an action in dependence upon a determination result.

Figure 4:
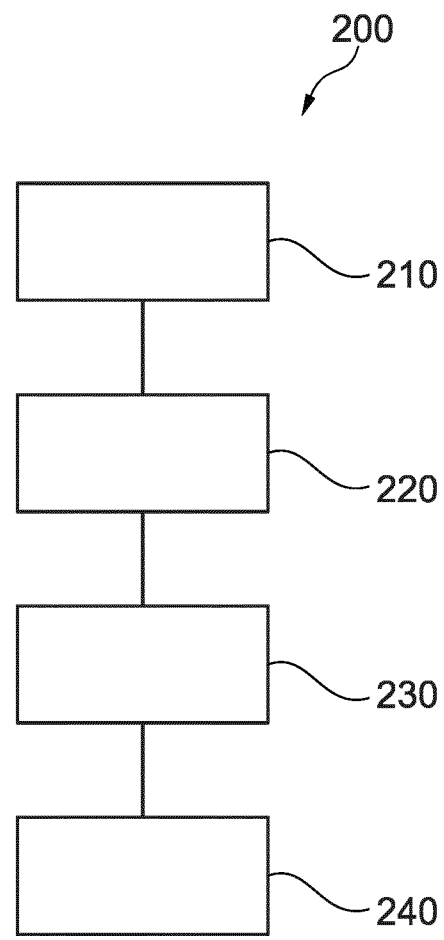
FIG. 4 schematically illustrates a method according to a third aspect of the present disclosure.
Figure 5:
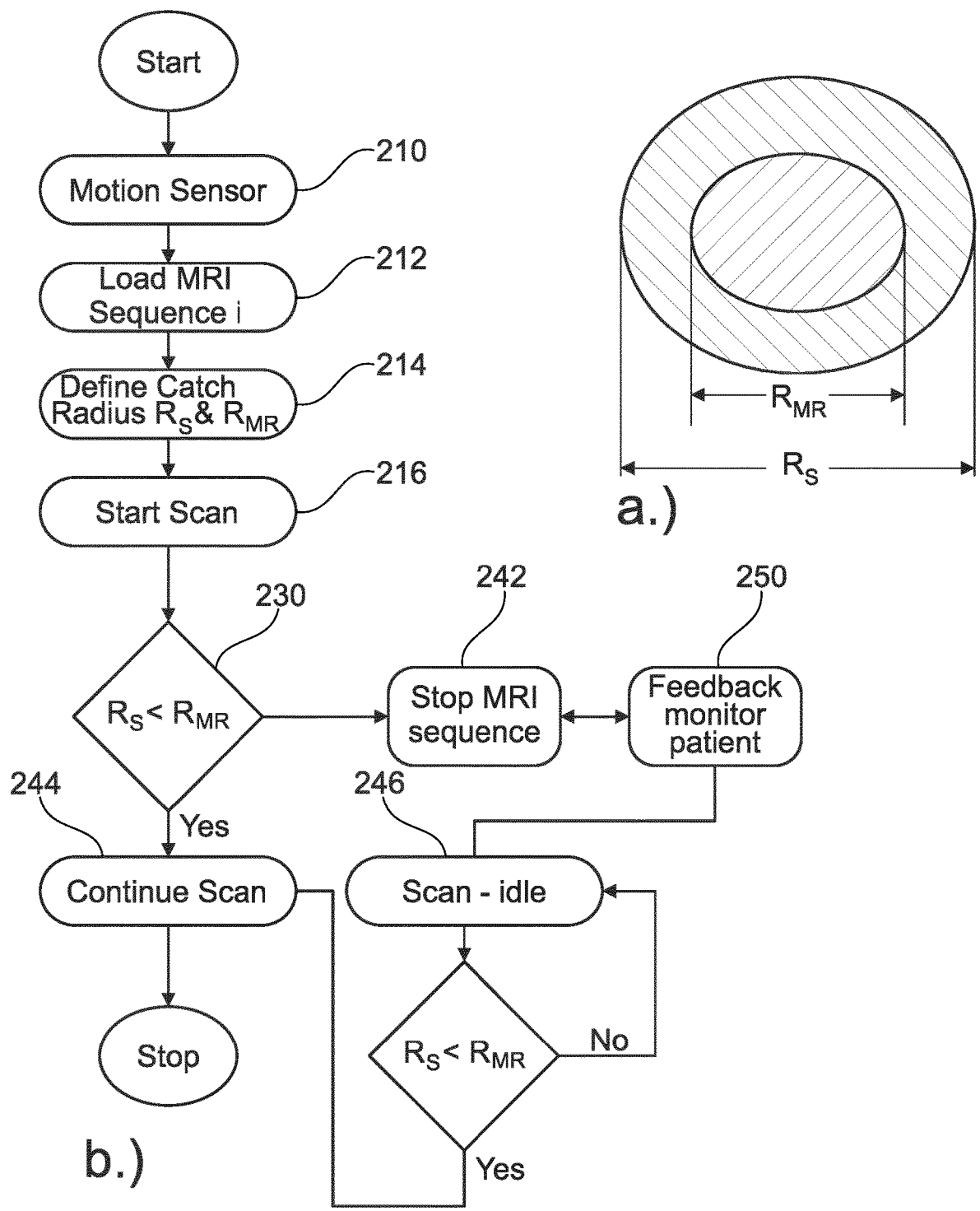
FIG. 5 schematically illustrates a method according to a further example.

FIG. 4 schematically illustrates the method 200 according to the third aspect. FIG. 5 schematically illustrates a further example of the method. As illustrated in FIG. 5b), a patient is located in a scanner, such as an MRI scanner.

In step 210, 3D contactless motion scanning e.g. using LIDAR, RADAR, or Video based sensing already provides information before the scan starts. This can happen already if the patient bed is still outside the bore of the scanner.

In step 212, information of motion statistics can be used to define parameters for the selection of MRI sequence regarding robustness against motion.

In step 214, a critical range, such as an individual critical catch radius parameter in FIG. 5, is determined based on a machine setting of the medical imaging system. As an example, the machine setting for an MRI system may include, but not limited to, slice-orientation, phase encoding direction, read-out bandwidth, K-space trajectory, and/or RF coil(s) being used.

Optionally, patient information, such as BMI, contour of patient, and/or patient ventilation volume, may serve as an optional input for the calculation of the critical range.

A pre-trained machine-learning model, such as convolutional neural-network (CNN), may be used to derive the critical range from the machine setting(s) and the optional patient information.

In step 216, when the patient is inside the MRI bore, the 3D sensing decides about the beginning of the sequence.

In step 230, during imaging the MRI sequence can compensate motion up to a catch radius $R_{MR}$.

If the motion parameter $R_S$ is below the catch radius $R_{MR}$, the sequence continues (step 244). If patient motion is too large and the motion parameter $R_S$ exceeds a critical catch radius $R_{MR}$, then the sequence is stopped (step 242). For example, FIG. 5a) illustrates a situation where the motion parameter $R_S$ exceeds the critical catch radius $R_{MR}$ The autonomous $M_{RI}$ scanner may hold in an idle mode (step 246). During that mode, the patient may be guided to retake its original position via a feedback system (step 250). The control loop calculates the catch radius deviation and the sequence is continued (latency) if condition is true.

It should also be understood that, unless clearly indicated to the contrary, in any methods claimed herein that include more than one step or act, the order of the steps or acts of the method is not necessarily limited to the order in which the steps or acts of the method are recited.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

All features can be combined to provide a synergetic effect that is more than the simple summation of the features.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A positioning apparatus for repositioning a body part of a patient when using a medical imaging system that comprises a medical imaging apparatus to perform a scan, the positioning apparatus comprising:
   a memory that stores a plurality of instructions; and
   processor circuitry that couples to the memory and is configured to execute the plurality of instructions to:
      obtain a first signal indicative of positional information of the body part of the patient that is being imaged in an imaging pose position;
      determine a critical range based on a machine setting of the medical imaging system using a pre-trained machine-learning model, within which a motion artefact is correctable with the medical imaging system;
      detect a change in the obtained first signal indicating a body motion of the patient;

determine whether a deviation of a position of the body part from the imaging pose position of the body part exceeds the determined critical range around the imaging pose position; and transmit a control signal to the medical imaging apparatus to cause the medical imaging apparatus to perform an action in dependence upon a determination result.

2. The positioning apparatus according to claim 1, wherein the processor circuitry is further configured to receive an other signal indicative of the machine setting of the medical imaging system and re-determine the critical range in response to a change of the other signal.

3. The positioning apparatus according to claim 1, wherein the processor circuitry is configured to determine the critical range based on patient information.

4. The positioning apparatus according to claim 1, wherein the critical range comprises at least one of:
a critical distance, if the deviation of a position of the body part from the imaging pose position of the body part comprises a one-dimensional motion vector;
a critical area, if the deviation of a position of the body part from the imaging pose position of the body part comprises a two-dimensional motion vector; and
a critical volume, if the deviation of a position of the body part from the imaging pose position of the body part comprises a three-dimensional motion vector.

5. The positioning apparatus according to claim 1, wherein the control signal comprises an interruption signal configured to be generated when it is determined that the deviation of the position of the body part from the imaging pose position of the body part exceeds the determined critical range around the imaging pose position; and wherein the interruption signal is configured to be transmitted to the medical imaging apparatus to cause the medical imaging apparatus to pause a scan process.

6. The positioning apparatus according to claim 1, wherein the control signal comprises a resume signal configured to be generated when it is determined that the body part is moved inside the determined critical range; and wherein the resume signal is configured to be transmitted to the medical imaging apparatus to cause the medical imaging apparatus to resume a scan process.

7. The positioning apparatus according to claim 1, wherein the processor circuitry is configured to compute a desired movement of the body part for moving the body part back to the imaging pose position or for moving the body part within the determined critical range around the imaging pose position, and transmit a corrective signal indicative of the desired movement to (i) an actuator to cause the actuator to effect the desired movement of the body part; and/or to (ii) an interactive reposition guidance device configured to advise the patient to effect the desired movement of the body part.

8. The positioning apparatus according to claim 1, wherein the processor circuitry is configured to obtain, via one or more sensors, a second signal indicative of a prospective indication of motion indicating that a body motion of the patient may happen, which triggers detection of the body motion of the patient.

9. A medical imaging system, comprising:
a medical imaging apparatus configured to perform a scan to acquire image data of a body part of the patient; and
an apparatus for repositioning a body part of a patient when using a medical imaging system to perform a scan, comprising:
a memory that stores a plurality of instructions; and
processor circuitry that couples to the memory and is configured to execute the plurality of instructions to:
obtain a first signal indicative of positional information of the body part of the patient that is being imaged in an imaging pose position;
determine a critical range based on a machine setting of the medical imaging system using a pre-trained machine-learning model, within which a motion artefact is correctable with the medical imaging system;
detect a change in the obtained first signal indicating a body motion of the patient;
determine whether a deviation of a position of the body part from the imaging pose position of the body part exceeds the determined critical range around the imaging pose position; and
transmit a control signal to the medical imaging apparatus to cause the medical imaging apparatus to perform an action in dependence upon a determination result.

10. The medical imaging system according to claim 9, wherein the medical imaging apparatus is a magnetic resonance imaging device; and wherein a B0 map inhomogeneity measurement is used for providing positional information of the body part of the patient that is being imaged.

11. The medical imaging system according to claim 9, further comprising:
one or more sensors configured to obtain the first signal indicative of positional information of the body part of the patient that is being imaged.

12. The medical imaging system according to claim 9, further comprising:
at least one actuator configured to effect a desired movement of the body part in response to a corrective signal.

13. The medical imaging system according to claim 9, further comprising:
an interactive reposition guidance device configured to advise the patient to effect a desired movement of the body part in response to a corrective signal.

14. A method for repositioning a body part of a patient when using a medical imaging system that comprises a medical imaging apparatus to perform a scan, comprising:
obtaining a first signal indicative of positional information of the body part of the patient that is being imaged in an imaging pose position;
detecting a change in the obtained first signal indicating a body motion of the patient;
determining a critical range based on a machine setting of the medical imaging system using a pre-trained machine-learning model, within which a motion artefact is correctable with the medical imaging system, whether a deviation of a position of the body part from the imaging pose position of the body part exceeds the determined critical range around the imaging pose position; and
transmitting a control signal to the medical imaging apparatus to cause the medical imaging apparatus to perform an action in dependence upon a determination result.

* * * * *